(12) United States Patent  
Blaha et al.

(10) Patent No.: US 7,259,340 B2
(45) Date of Patent: Aug. 21, 2007

(54) ILLUMINATED FOOT-SWITCH

(75) Inventors: Derek M. Blaha, Longmont, CO (US); William N. Gregg, Superior, CO (US)

(73) Assignee: Sherwood Services AG, Schaffhausen (CH)

( * ) Notice: Subject to any disclaimer, the term of this patent is extended or adjusted under 35 U.S.C. 154(b) by 28 days.

(21) Appl. No.: 10/516,865

(22) PCT Filed: May 29, 2003

(86) PCT No.: PCT/US03/17126

§ 371 (c)(1), (2), (4) Date: Aug. 5, 2005

(87) PCT Pub. No.: WO03/105169

PCT Pub. Date: Dec. 18, 2003

(65) Prior Publication Data

US 2006/0090990 A1 May 4, 2006

Related U.S. Application Data

(60) Provisional application No. 60/388,658, filed on Jun. 11, 2002.

(51) Int. Cl.
H01H 9/20 (2006.01)
H01H 3/14 (2006.01)

(52) U.S. Cl. ...................... 200/310; 200/86.5
(58) Field of Classification Search ............. 200/52 R, 200/85 R, 86.5, 310–317
See application file for complete search history.

(56) References Cited

U.S. PATENT DOCUMENTS

| 4,417,875 | A | 11/1983 | Matsui |
| 5,166,513 | A | 11/1992 | Keenan et al. |
| 5,180,925 | A * | 1/1993 | Lieb ........................... 307/114 |
| 5,635,777 | A * | 6/1997 | Telymonde et al. ......... 307/119 |
| 5,712,460 | A | 1/1998 | Carr et al. |
| 5,863,112 | A * | 1/1999 | Didato ....................... 362/488 |
| 5,883,615 | A | 3/1999 | Fago et al. |
| 6,051,797 | A | 4/2000 | Meinel |
| 6,176,853 | B1 | 1/2001 | Stolyarenko |
| 6,179,614 | B1 | 1/2001 | Elrod et al. |
| 6,179,829 | B1 | 1/2001 | Bisch et al. |
| 6,360,630 | B2 | 3/2002 | Holtorf |
| 6,452,123 | B1 | 9/2002 | Chen |
| 6,608,267 | B2 | 8/2003 | Fischer et al. |
| 6,639,332 | B2 | 10/2003 | Metzler et al. |
| 6,674,030 | B2 | 1/2004 | Chen et al. |
| 6,689,975 | B2 | 2/2004 | Metzler et al. |
| 6,866,507 | B2 | 3/2005 | Beerstecher |
| 6,894,236 | B2 * | 5/2005 | Chappuis ................... 200/86.5 |
| 6,962,581 | B2 | 11/2005 | Thoe |
| 6,969,811 | B1 * | 11/2005 | Lai ........................... 200/86.5 |
| 7,012,203 | B2 | 3/2006 | Hanson et al. |
| 7,083,608 | B2 | 8/2006 | Tomita et al. |
| 7,094,231 | B1 | 8/2006 | Ellman et al. |
| 7,122,751 | B1 * | 10/2006 | Anderson et al. ......... 200/85 R |

(Continued)

Primary Examiner—Michael A Friedhofer

(57) ABSTRACT

A control system for an electrosurgical instrument includes a housing selectively positionable relative to an operating theater with the housing being coupled to an electrosurgical energy source. The system also includes at least one foot-activatable pedal operatively engaged with the housing which has indicia identifying the function of the pedal disposed thereon. Illuminating means are also included with the system which illuminating means are designed to illuminate at least a portion of the pedal which, in turn illuminates the indicia.

11 Claims, 6 Drawing Sheets

U.S. PATENT DOCUMENTS

| | | |
|---|---|---|
| 2002/0045887 A1 | 4/2002 | DeHoogh et al. |
| 2003/0051985 A1 | 3/2003 | Chen et al. |
| 2003/0073980 A1 | 4/2003 | Finlay et al. |
| 2004/0106915 A1 | 6/2004 | Thoe |
| 2005/0143724 A1 | 6/2005 | El-Galley et al. |

* cited by examiner

ID FOOT-SWITCH

CROSS-REFERENCE TO RELATED APPLICATIONS

The present application claims the benefit of and priority to International Application Serial No. PCT/US03/17126, filed on May 29, 2003, which claims the benefit of and priority to U.S. Provisional Patent Application No. 60/388, 658 filed on Jun. 11, 2002, the entire contents of which are incorporated herein by reference.

BACKGROUND

1. Technical Field

The present disclosure relates to a foot-activated control switch and, more particularly, to an illuminated foot-activated control switch for use during a surgical procedure and, even more particularly, to an illuminated foot-activated control switch for use in a darkened operating room during a surgical procedure.

2. Background of Related Art

Many surgical devices today are configured to perform a variety of different selectable functions or operations. Such multi-function devices are typically equipped with some kind of control mechanism to allow an operator to select and actuate a particular function of the device from an array of functions which the device is capable of performing.

In the past, control mechanisms or control units were typically hand-held and included a plurality of switches which were depressed by the operator in order to actuate and/or perform the various functions available in the multi-function device. However, a hand-held control unit requires that the operator interrupt the on-going medical/surgical procedure in order to actuate the various functions of the multi-functional device as needed. In the least, a hand-held control unit requires that one hand of the operator be free in order to manipulate the control unit and actuate one or more switches. As may be appreciated, it is undesirable and often difficult for the operator to have one hand free to manipulate and control hand-actuated switches.

Recently, one solution that has been offered as an alternative to a hand control unit is a foot-operated control system having a variety of engageable devices such as buttons, pedals or joysticks which may be manipulated by the operator's feet thereby leaving the operator's hands free to perform other tasks during a surgical procedure. While foot-operated control systems have been suitable for a variety of different apparatus, such control systems have generally been limited to the types of surgical procedures in which the foot operated control system can be utilized. Various considerations must be taken into account when utilizing a foot-operated system including the size of the system, its mobility, the positioning of the actuation devices within the system, and the visibility of the foot-operated control system in a darkened operating room during a surgical procedure.

The dexterity of an operator with respect to his/her feet is much more cumbersome compared to hand dexterity, especially when the operator is wearing shoes, as will normally be the case. As such, the actuation devices of the system (i.e., the pedals) are generally appropriately sized and spaced for suitable actuation by a foot without the inadvertent actuation of other functions of the system.

Moreover, during many surgical procedures, the operating rooms are typically dark. As a result, if the operator should move his/her foot off of the foot-operated control system or if the foot-operated control system should be inadvertently moved, it is important for the operator to quickly locate the control system and properly place his/her foot on the appropriate actuation pedal as needed. Should the operator errantly place his/her foot on the incorrect or undesired actuation pedal, the operator may accidentally actuate the incorrect function on the multi-function device which may prove traumatic.

Increasing the overall size of the foot-operated control system has been advanced as a possible suitable solution. However, in a darkened operating room, the operator may still not be able to discern which actuation pedal to actuate even if the operator is looking in the direction of the foot control system. Accordingly, the need exists for a foot-operated control system or switch having illuminated or otherwise discernible foot-activated pedals which are readily recognizable by an operator in a darkened operating room.

SUMMARY AND OBJECTS

The foot-activated control system of the present disclosure is operably coupled to an electrosurgical instrument in order to selectively actuate one of a number of selectable functions of the electrosurgical instrument. In one embodiment of the disclosure, the control system includes a housing selectively positionable relative to an operating theater with the housing being coupled to an electrosurgical energy source. At least one foot-activatable pedal is operatively engaged with the housing, which includes indicia identifying the function of the pedal. The control system also includes means for illuminating at least a portion of the pedal which, in turn illuminates the indicia.

In an alternative embodiment of the disclosure, the control system includes a pair of foot-activatable pedals operatively engaged with the housing; a first of the pair of foot-activatable pedals controlling a first function of the electrosurgical instrument and a second of the pair of foot-activatable pedals controlling a second function of the electrosurgical instrument. Means are included to illuminate each of the pair of foot-activatable pedals.

Preferably, the illuminating means associated with a particular pedal blinks upon actuation of the respective foot-activatable pedal.

In still another embodiment of the disclosure, the control system includes first means for illuminating the first of the pair of foot-activatable pedals and second means for illuminating the second of the pair of foot-activatable pedals. Preferably, the first illuminating means includes a first color selected from a group consisting of red, yellow, green, blue and white and the second illuminating means includes a second, different, color selected from the group consisting of red, yellow, green, blue and white. It is envisioned that any combination of contrasting, readily discernible colors may be utilized to accomplish this purpose.

In another embodiment of the present disclosure, the foot-activatable pedals include an arm portion and the indicia are formed by a plurality of light-emitting diodes disposed atop each of the arm portions. In yet another embodiment, each of the foot-activatable pedals includes a foot rest formed at one end thereof and each of the foot rests includes a plurality of light-emitting diodes affixed about an outer periphery thereof.

Preferably, the indicia are formed in an upper surface of a respective foot-activatable pedal wherein the illuminating means will cause the indicia to illuminate from within each foot-activatable pedal. Alternatively, the indicia are dimensioned as a groove formed in an upper surface of a respective foot-activatable pedal and the groove includes a transparent or translucent material disposed therein.

In another embodiment of the present disclosure, each of the first and second foot-activatable pedals includes a foot rest formed at a distal end thereof with a foot pad disposed on an upper surface of the foot rest. The foot rest includes a groove which surrounds the foot pad formed in the upper surface thereof. The groove can be provided with a transparent or a translucent material disposed therein which "glows" upon activation of the illuminating means.

These and other objects will be more clearly illustrated below by the description of the drawings and the detailed description of the preferred embodiments.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION

Figure 1:
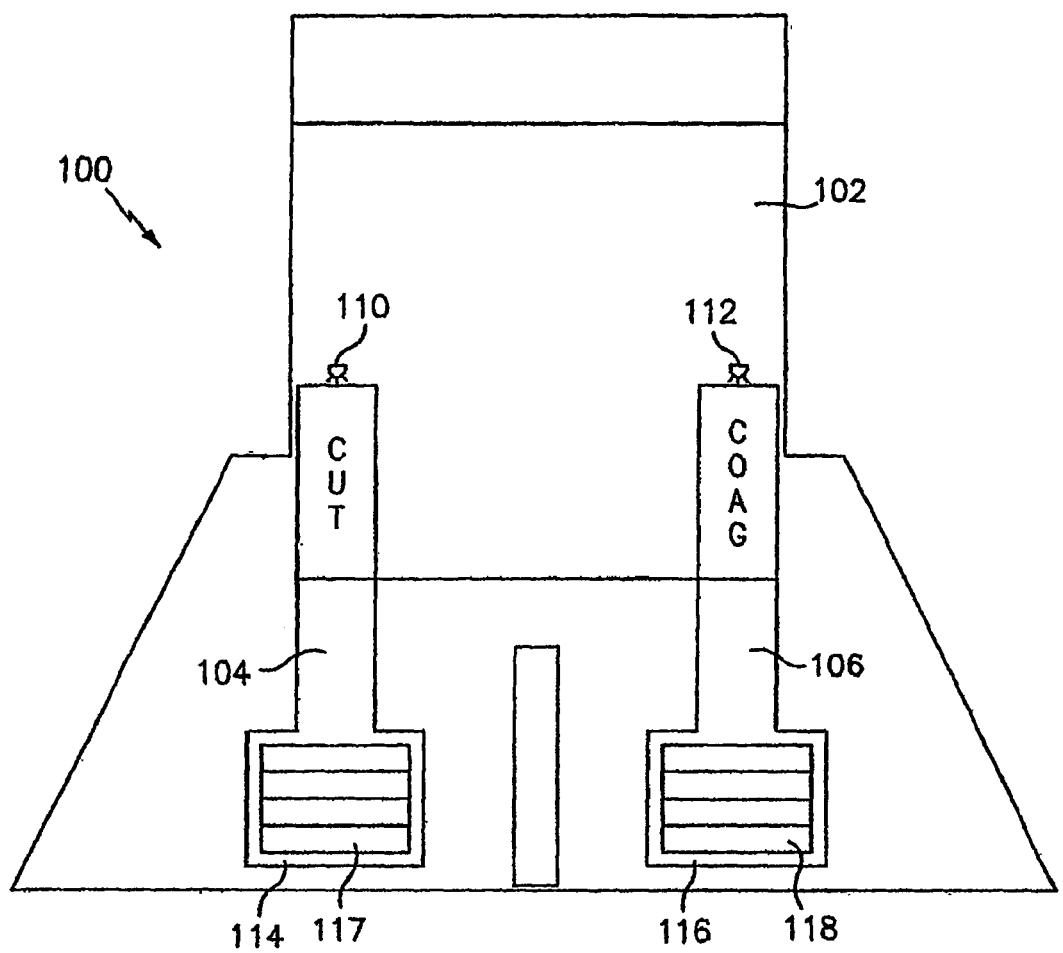
FIG. 1 is a top plan view of an illuminated foot-activatable control switch in accordance with the present disclosure.

Preferred embodiments of the presently disclosed illuminated foot-activated control switch will now be described in detail with reference to the drawing figures wherein like reference numerals identify similar or identical elements. The illuminated foot-activated control switch as shown herein is described as actuating an electrosurgical instrument which can perform many different functions, e.g., cutting (i.e., referred to as "CUT" in the figures), coagulating (i.e., referred to as "COAG" in the figures) and sealing (i.e., "SEAL" in the figures). While only certain functions are shown in the figures it is within the scope of the present disclosure that any electrosurgical instrument can be operatively coupled to the illuminated foot-activated control switch and be actuated by a corresponding control switch.

Figure 2:
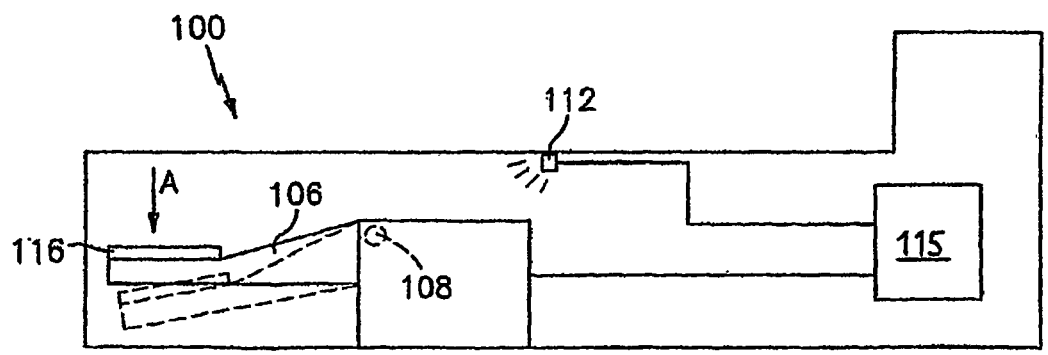
FIG. 2 is a side elevational view of the illuminated control switch shown in FIG. 1 with actuation of the foot pedal shown in phantom.

Referring now in detail to FIGS. 1 and 2, an illuminated foot-activated control switch is shown in accordance with the present disclosure and is generally identified as 100. Foot switch 100 includes a housing 102 and first and second foot activatable pedals 104 and 106, respectively, which are each pivotably coupled to housing 102 at a proximal end via a pivot pin 108. Each foot pedal 104 and 106 is electrically coupled to light emitting diode (LED) 110 and 112, respectively, which is, in turn electrically coupled to a power source 115. Each foot pedal 104 and 106 includes a foot rest 114 and 116, respectively, formed at one end thereof and each foot rest 114 and 116 has a corresponding foot pad 117 and 118 disposed on an upper surface thereof. As best shown in FIG. 1, the upper surface of first pedal 104 includes the term "CUT" thereon and the upper surface of second pedal 106 includes the term "COAG" thereon. Preferably, each of the terms, i.e., "CUT" and "COAG", is inscribed atop a facing surface of the respective foot pedal such that, when illuminated, a surgeon can easily and readily discern a particular pedal prior to and/or during activation.

LED's 110 and 112 are mounted to housing 102, preferably at a point proximal to and above the foot pedals 104 and 106. In this manner, foot pedals 104 and 106 and their corresponding indicia "CUT" and "COAG" are illuminated by LED's 110 and 112 respectively. Accordingly, while performing a surgical procedure in a darkened operating room, each foot pedal 104 and 106 and the respective indicia "CUT" and "COAG" displayed thereon is illuminated such that an operator can quickly and readily identify which foot pedal 104 and 106 he/she wishes to actuate in order to perform a desired function of the electrosurgical instrument.

It is envisioned that LEDs 110 and 112 are illuminated prior to activation such that each pedal 104 and 106 is readily discernible. However, it is contemplated that LED 112 can also illuminate each pedal upon actuation, intensify each pedal upon actuation, blink repeatedly upon actuation or audibly sound upon actuation.

Figure 3A:
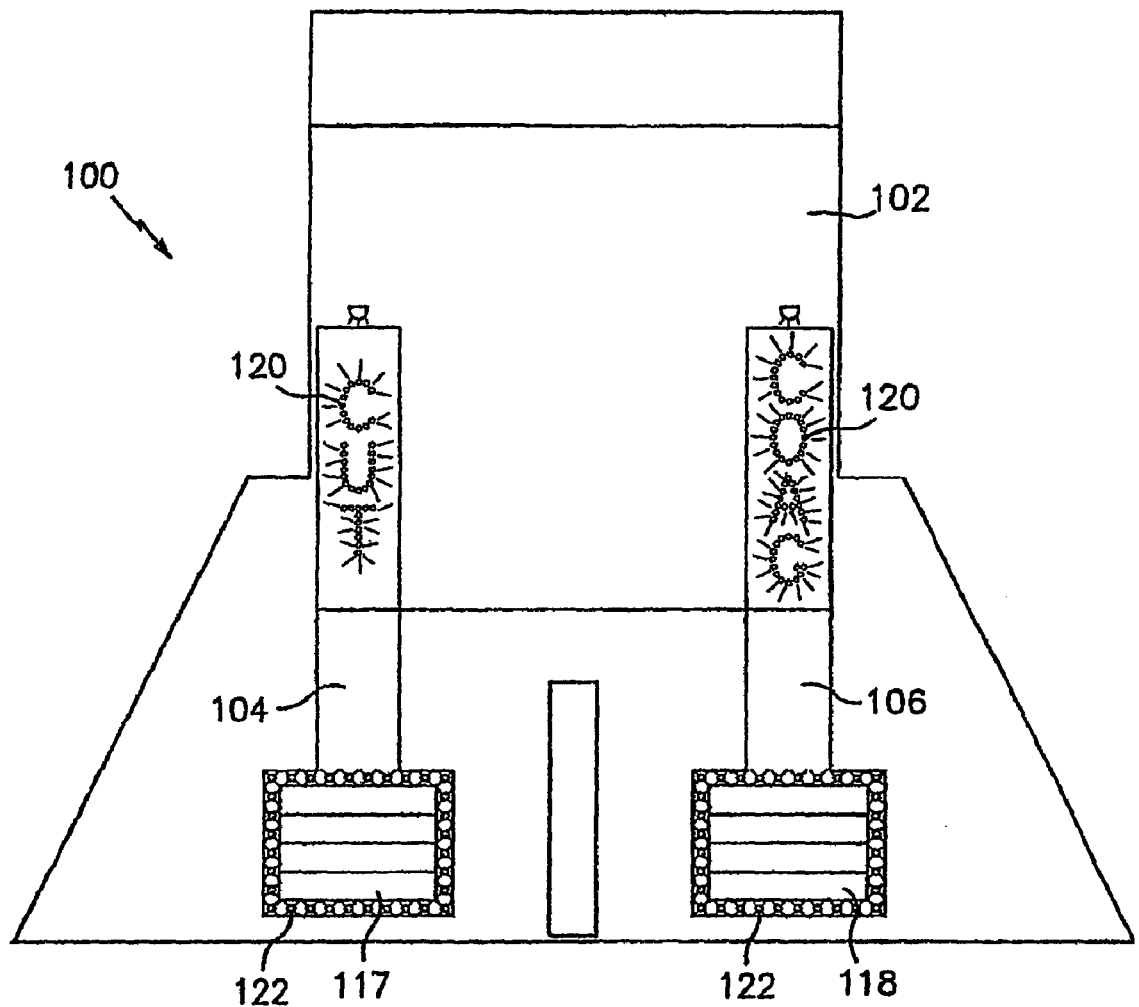
FIG. 3A is a top plan view of an illuminated control switch in accordance with an alternative embodiment of the present disclosure.

Turning now to FIG. 3A, another embodiment of the foot switch 100 is shown wherein the terms "CUT" and "COAG" are formed from a plurality of LEDs 120. Each foot rest 114 and 116 also includes a plurality of LEDs 122 outlining pads 117 and 118. As can be appreciated, when the operator looks down at foot switch 100, the indicia "CUT" and "COAG" as well as the perimeter of each foot pad 117 and 118 will be illuminated by LEDs 120 and 122, respectively. In this manner, the operator can quickly ascertain precisely which foot pedal 104 and 106 to depress in order to actuate the desired function of the electrosurgical instrument.

Figure 3B:
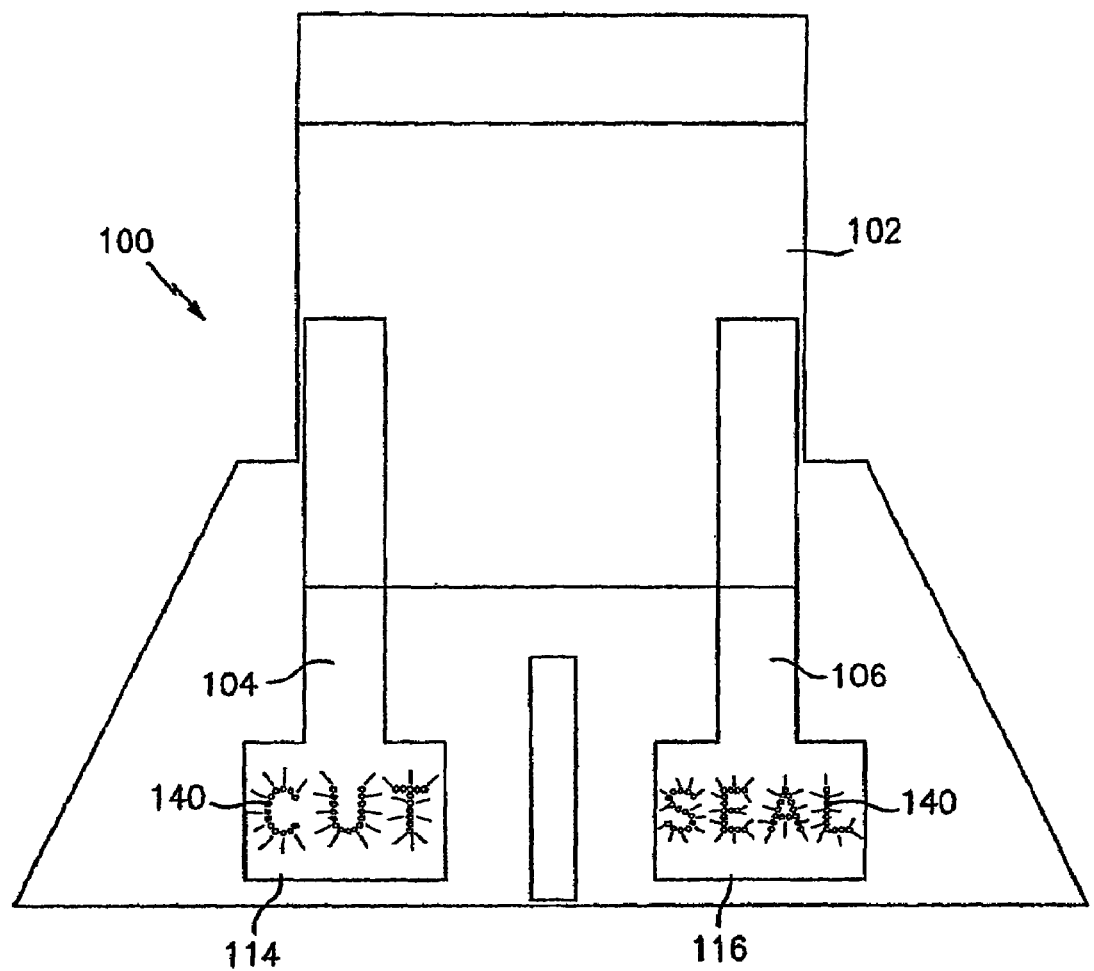
FIG. 3B is a top plan view of an illuminated control switch in accordance with an alternative embodiment of the present disclosure.

Turning now to FIG. 3B, an alternative embodiment of illuminated foot switch 100 is shown in which the upper surface of foot rests 114 and 116 are each provided with the term "CUT" and "SEAL", respectively. The terms "CUT" and "SEAL" are formed from a plurality of LEDs 140 respectively. In this manner, when the operator looks down at the foot pedal, e.g., 104, the foot rest identifies the feature available on the electrosurgical instrument.

Figure 4:
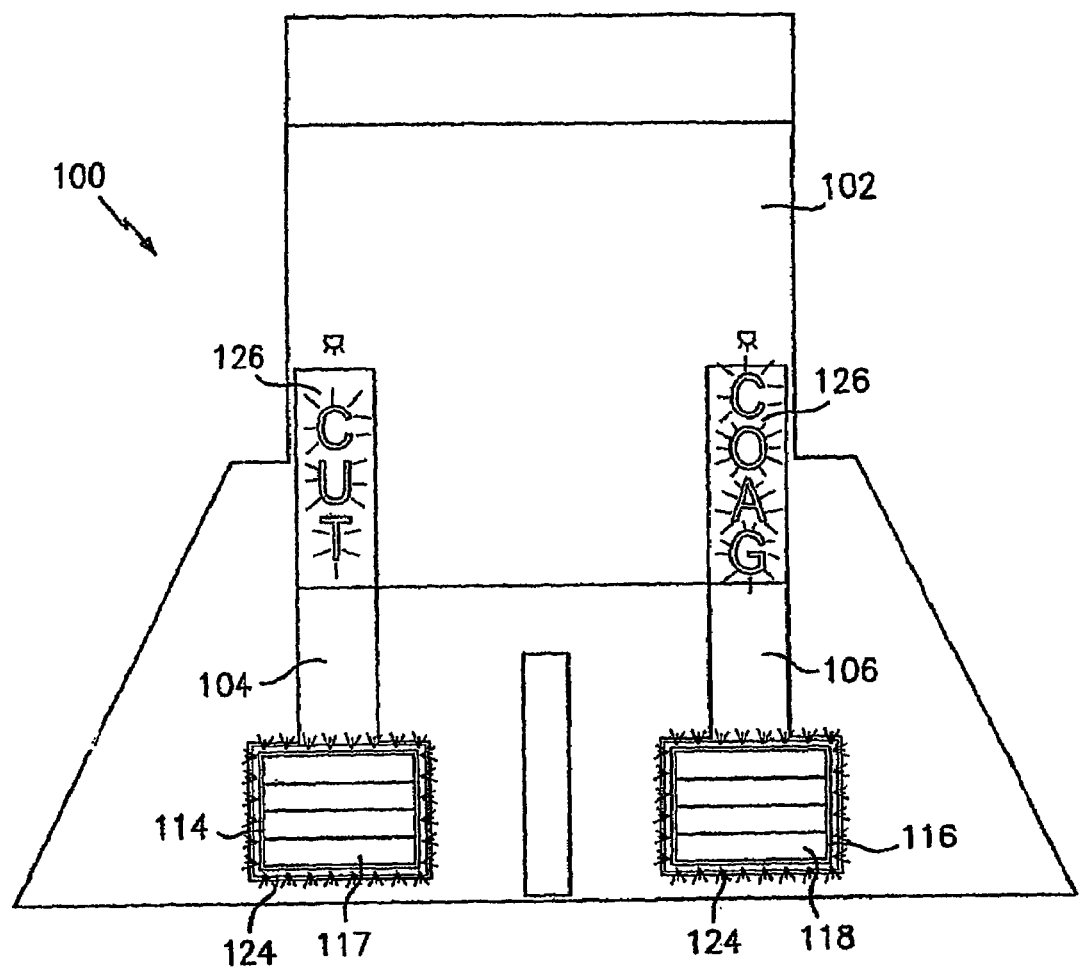
FIG. 4 is a top plan view of an illuminated control switch in accordance with an alternative embodiment of the present disclosure.

FIG. 4 shows another embodiment of the foot switch 100 wherein the terms "CUT" and "COAG" are made up of either a translucent material (i.e., plastic) or a transparent material (i.e., glass or clear plastic) which glows upon illumination. Each foot rest 114 and 116 is provided with a channel 124 encircling pads 117 and 118 also having a translucent or transparent material disposed therein. In this manner, the light source 110, 112 illuminates both the indicia and the corresponding foot pedal 104 and 106. It is also envisioned that a separate light source (not shown) can be disposed within each individual pedal 104 and 106 to cause the indicia "CUT" and "COAG" (as well as channel 124) to illuminate from within. Again, the operator can readily discern which pedal to depress in order to actuate the desired function of the electrosurgical instrument.

Figure 5:
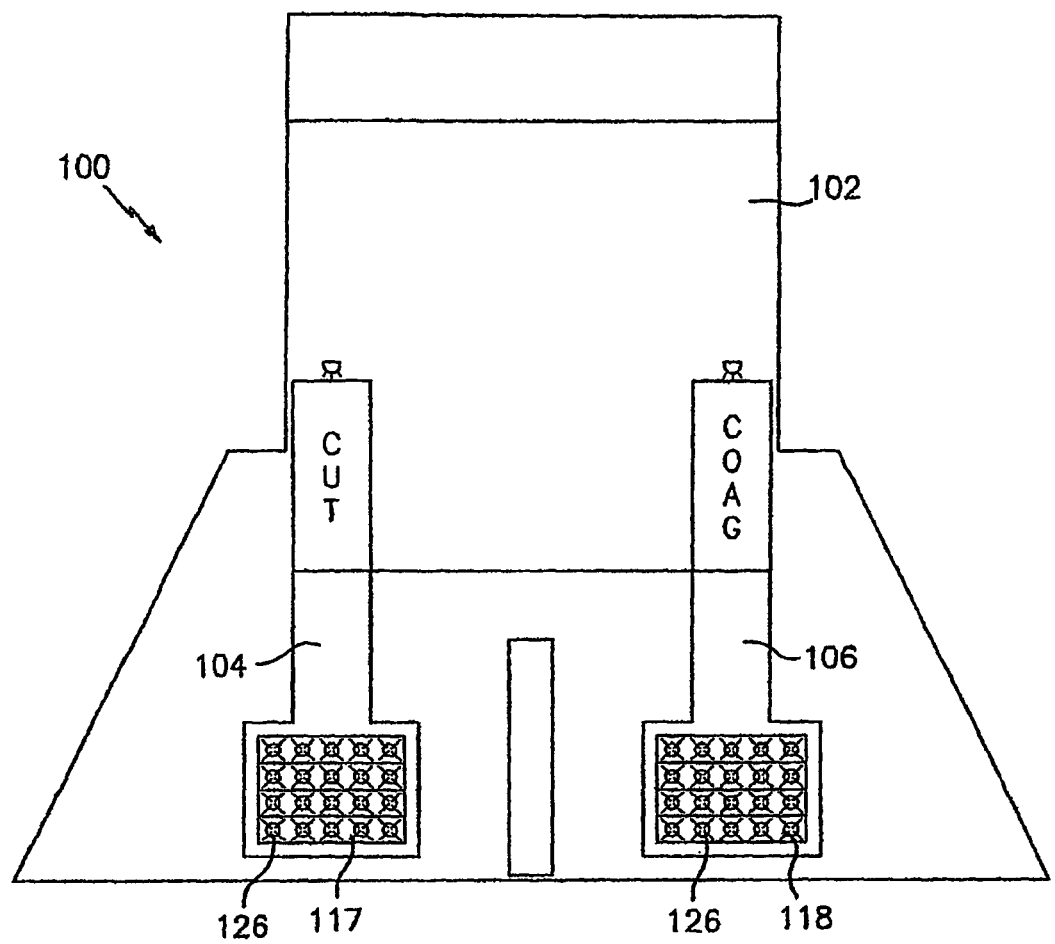
FIG. 5 is a top plan view of an illuminated control switch in accordance with an alternative embodiment of the present disclosure.
Figure 6:
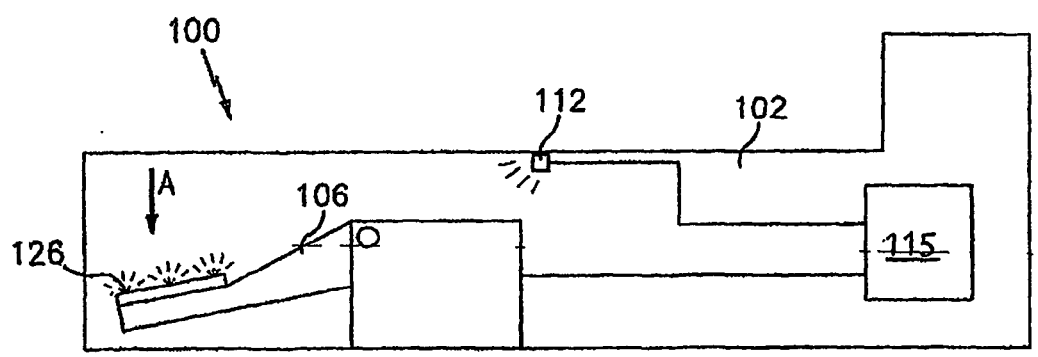
FIG. 6 a side elevational view of an illuminated control switch of FIG. 5.

Turning now to FIGS. 5 and 6, an alternative embodiment of the foot switch 100 is shown in which each foot pad 117 and 118 includes a plurality of LEDs 126. Each foot pedal 104 and 106 is illuminated by a corresponding LED 110 and 112, respectively, mounted to housing 102 and each foot pad 117 and 118 is illuminated by LEDs 126. If desired, LEDs 110, 112 and 126 can be electrically coupled to an electrical switch (not shown) such that when foot pedals 104 and 106 are depressed, LEDs 110, 112 and 126 blink (see FIG. 6), indicating to the operator or to the operating room staff that the multi-functional instrument is activated. While the blinking feature of the LEDs has been disclosed with the present embodiment, it is envisioned that any of the above described embodiments can be provided with an electrical switch, connected between the foot pedals and the corresponding LEDs, which will cause the LEDs to blink upon actuation of a respective foot activatable pedal. Alternatively, the LEDs can be coupled to an audible switch which rings or chirps upon activation and/or deactivation of a foot pedal 104, 106.

Preferably, the LEDs are all the same color, however, it is contemplated that the LEDs may be different colors in order to aid the operator in distinguishing one foot pedal from the next. For example, in FIGS. 1 and 2, LED 110 can be one of either red, yellow, green, blue or white while LED 112 is another of either red, yellow, green, blue or white. Preferably, when using multiple colors, the colors contrast one another for facile recognition among pedals. In this manner, each foot pedal 104 and 106 is illuminated in a different color thereby further differentiating foot pedal 104 from foot pedal 106. Likewise, in the embodiment of FIG. 3, LEDs 120 and 122 of each foot pedal 104 and 106 can include differently colored LEDs. It is also envisioned that the terms "CUT" and "COAG" as well as their respective channels 124 can be back lit by a differently colored LED. Likewise, in the embodiment shown in FIG. 6, LEDs 126 which form foot pads 117 and 118, can include differently colored LEDs respectively.

While each of the above described embodiments relates to a foot-activated control switch having two foot-activatable pedals, any number of foot-activatable pedals can be provided wherein each foot-activatable pedal actuates a different function of the electrosurgical instrument.

It will be understood that various modifications may be made to the embodiments of the presently disclosed foot switch disclosed herein. For example, all of the LEDs may be constantly illuminated, i.e., while a foot pedal is being actuated or while the foot pedal is idle. Alternatively, LEDs can commence blinking upon activation or non-activated LEDs can go out upon the actuation of a corresponding, i.e., "selected," foot pedal.

Figure 7:
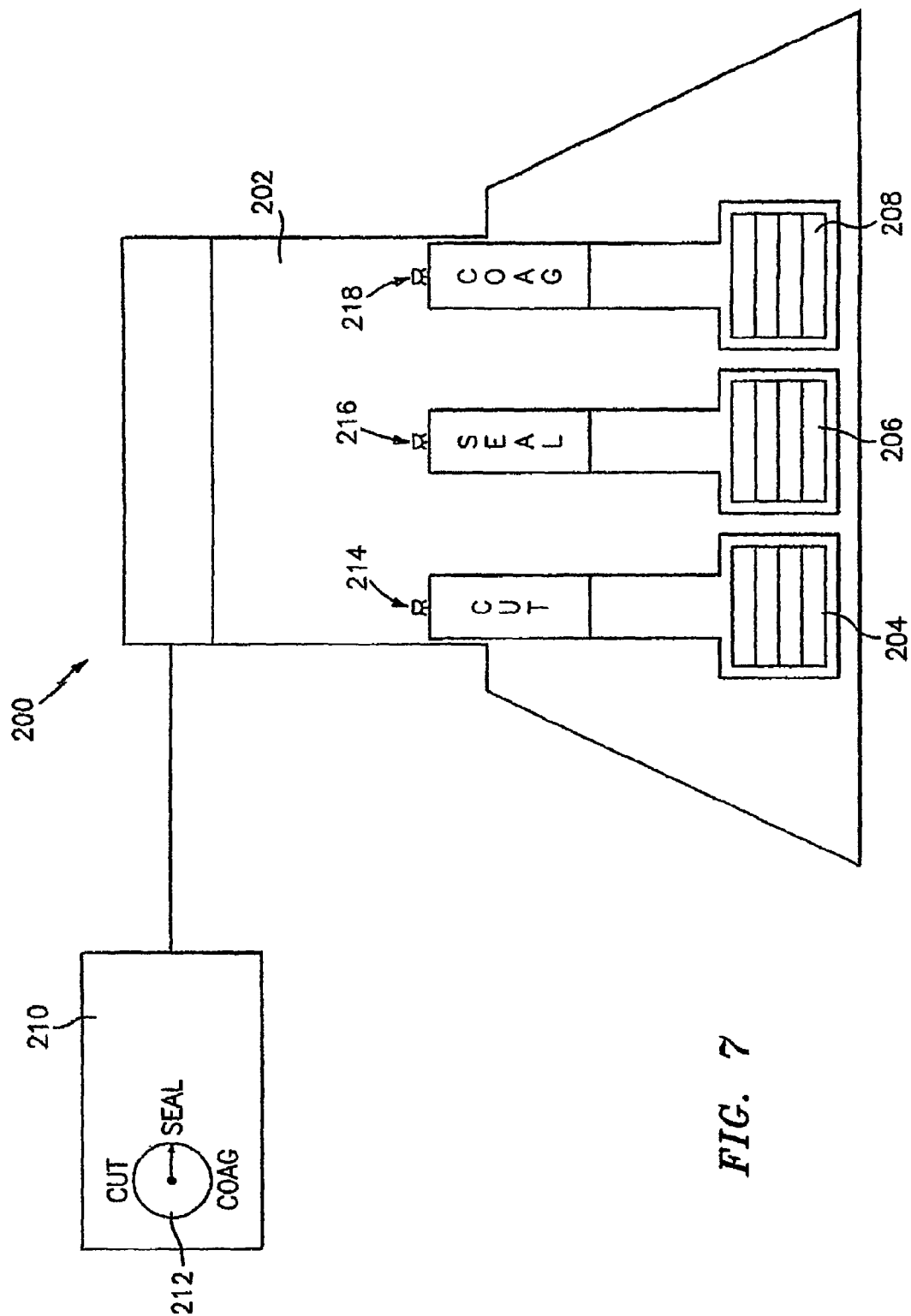
FIG. 7 is a schematic view of an alternative embodiment of an illuminated control switch according to the present disclosure shown connected to an electrosurgical generator.

FIG. 7 shows another embodiment of the presently disclosed illuminated foot switch 200 which includes housing 202 and a first, second and third foot pedal 204, 206 and 208, respectively. Each pedal 204, 206 and 208 is pivotably coupled to housing 202 about a proximal end and is provided with indicia "CUT", "SEAL" and "COAG" inscribed thereon, respectively. Foot switch 200 is provided with LEDs 212, 214 and 216 which are designed to illuminate a corresponding pedal 204, 206 and 208, respectively.

Each pedal 204, 206 and 208 together with its corresponding LEDs 214, 216 and 218 is coupled to an electrosurgical generator 210 which includes a "selector" 212 for selectively setting generator 210 to either "CUT", "SEAL" or "COAG." When the selector 212 is set to one of the modes, e.g., "SEAL", a corresponding LED 216 turns on, thus illuminating the corresponding pedal 206. As can be appreciated, this allows the surgeon to readily depress the corresponding pedal to activate the sealing function of an electrosurgical instrument.

Alternatively, the foot switch 200 may include a screen-like display (not shown) atop the foot pedals 204, 206 and 208 which illuminates and forms the particular functions selected by the surgeon, for example, the electrosurgical generator 210 may include three or four selectable functions and the foot switch may have two pedals. When the surgeon selects two functions on the generator 210, the foot switch displays/illuminates these functions. As can be appreciated, this allows the same foot switch 200 to be used with any combination of functions.

Therefore, the above description should not be construed as limiting, but merely as exemplifications of preferred embodiments. Those skilled in the art will envision other modifications within the scope and spirit of the present disclosure.

What is claimed is:

1. A control system for an electrosurgical instrument, comprising:
   a housing selectively positionable relative to an operating theater, the housing coupled to an electrosurgical energy source;
   a pair of foot-activatable pedals operatively engaged with the housing, a first of the pair of foot-activatable pedals controlling a first function of the electrosurgical instrument and a second of the pair of foot-activatable pedals controlling a second function of the electrosurgical instrument, each of the pair of foot-activatable pedals including indicia identifying corresponding first and second functions of the electrosurgical instrument, wherein each of the pair of foot-activatable pedals includes an arm portion and wherein the indicia is formed by a plurality of light-emitting diodes disposed atop each of the arm portions; and
   means for illuminating at least a portion of each of the pair of foot-activatable pedals.

2. A control system for an electrosurgical instrument comprising:
   a housing selectively positionable relative to an operating theater, the housing coupled to an electrosurgical energy source;
   a pair of foot-activatable pedals operatively engaged with the housing, a first of the pair of foot-activatable pedals controlling a first function of the electrosurgical instrument and a second of the pair of foot-activatable pedals controlling a second function of the electrosurgical instrument, each of the pair of foot-activatable pedals including indicia identifying corresponding first and second function of the electrosurgical instrument, wherein each of the pair of foot-activatable pedals includes a foot rest formed at one end thereof, each of said foot rests including a plurality of light-emitting diodes affixed about an outer periphery thereof; and
   means for illuminating at least a portion of each of the pair of foot-activatable pedals.

3. A control system according to claim 2, wherein said control system includes:
   first means for illuminating said first of said pair of foot rests; and
   second means for illuminating said second of said pair of foot rests.

4. A control system according to claim 3, wherein said first illuminating means includes a first color selected from a group consisting of red, yellow, green, blue and white; and wherein said second illuminating means includes a second color, different from said first color, and selected from a group consisting of red, yellow, green, blue and white.

5. A control system according to claim 2, wherein said indicia is formed in an upper surface of a respective foot-activatable pedal, and wherein illuminating means disposed within each foot-activatable pedal will cause said indicia to illuminate from within each foot-activatable pedal.

6. A control system according to claim 2, wherein each of said first and second foot-activatable pedals further comprises a foot pad disposed on an upper surface of said foot rest and groove surrounding said foot pad is formed in said upper surface of said foot rest.

7. A control system according to claim 6, wherein said groove has one of a transparent and a translucent material disposed therewithin, wherein illuminating means disposed within each foot rest will illuminate said foot rest from within.

8. A control system according to claim 6 wherein said control system includes:
   first means for illuminating said groove of said foot rest of said first foot-activatable pedal; and
   second means for illuminating said groove of said foot rest of said second foot-activatable pedal.

9. A control system according to claim 8, wherein each of said first and second illuminating means blinks upon an actuation of one of said first and second foot-activatable pedals.

10. A control system for an electrosurgical instrument, comprising:
   a housing selectively positionable relative to an operating theater, the housing coupled to an electrosurgical energy source;
   at least one foot-activatable pedal operatively engaged with the housing, the at least one pedal including indicia identifying a function of the at least one pedal, wherein the at least one foot-activatable pedal includes a foot rest formed at one end thereof, the foot rest having a foot pad disposed on an upper surface thereof, the foot pad including a plurality of light-emitting diodes affixed thereto such that each foot pad is separately illuminated; and
   means for illuminating at least a portion of the at least one pedal to illuminate the indicia.

11. A control system for an electrosurgical instrument, comprising:
   a housing selectively positionable relative to an operating theater, said housing coupled to an electrosurgical energy source;
   at least one foot-activatable pedal operatively engaged with said housing, each of said foot-activatable pedals including:
   an arm portion having indicia identifying a function of each of the foot-activatable pedals formed by a plurality of light emitting diodes disposed atop each of said arm portions; and
   a foot rest formed at one end thereof, wherein each of said foot rests include a plurality of light-emitting diodes affixed about an outer periphery thereof; and
   means for illuminating at least a portion of each of said pedals to illuminate said indicia.

* * * * *